(12) United States Patent
Turk et al.

(10) Patent No.: US 11,896,258 B2
(45) Date of Patent: Feb. 13, 2024

(54) ACTIVE CUTTING CATHETER WITH HOUSED EXPANDABLE ACTUATOR

(71) Applicant: C.R. BARD, INC., Tempe, AZ (US)

(72) Inventors: Lauren Turk, Phoenix, AZ (US); Brandon Simmons, Tempe, AZ (US); Mark Nicholas Wright, Gilbert, AZ (US)

(73) Assignee: C.R. BARD, INC., Franklin Lakes, NJ (US)

( * ) Notice: Subject to any disclaimer, the term of this patent is extended or adjusted under 35 U.S.C. 154(b) by 163 days.

(21) Appl. No.: 17/266,683

(22) PCT Filed: Feb. 28, 2019

(86) PCT No.: PCT/US2019/019942
§ 371 (c)(1),
(2) Date: Feb. 8, 2021

(87) PCT Pub. No.: WO2020/176091
PCT Pub. Date: Sep. 3, 2020

(65) Prior Publication Data
US 2021/0378701 A1    Dec. 9, 2021

(51) Int. Cl.
*A61B 17/3207*    (2006.01)
(52) U.S. Cl.
CPC .............. *A61B 17/32075* (2013.01); *A61B 17/320783* (2013.01); *A61B 2017/320791* (2013.01)
(58) Field of Classification Search
CPC ...... A61B 17/32075; A61B 17/320783; A61B 2017/320791; A61B 17/320725;
(Continued)

(56) References Cited

U.S. PATENT DOCUMENTS 4,721,103 A    1/1988  Freedland
5,645,529 A *  7/1997  Fagan ................ A61M 25/1011
                                              604/101.01
(Continued)

FOREIGN PATENT DOCUMENTS

EP    834287 A1    4/1998
JP    H1094543 A   4/1998
JP    2006515789 A 6/2006

OTHER PUBLICATIONS

"Contact." Merriam-Webster.com Dictionary, Merriam-Webster, https://www.merriam-webster.com/dictionary/contact. Accessed Apr. 4, 2023.*

*Primary Examiner* — Brooke Labranche
*Assistant Examiner* — Lauren Dubose
(74) *Attorney, Agent, or Firm* — Dickinson Wright PLLC; Andrew D. Dorisio (57) ABSTRACT

An apparatus for cutting a wall of a vessel, such as scoring or slicing a lesion associated therewith. A catheter (10) includes a shaft (12) having a distal portion supporting a housing (20) including a first lateral passage (20a). A cutter (22) is adapted for moving from a retracted position within the housing (20) to a deployed position for at least partially projecting from the passage (20a). A expandable actuator (24) within the housing (20), such as an inflatable balloon (26), actuates the cutter (22) to move from the retracted position fully within the housing (20) to the deployed position at least partially projecting from the housing (20). More than one cutter (22') may be provided, which cutters (22') may be simultaneously actuated by the same actuator (26').

13 Claims, 5 Drawing Sheets

(58) Field of Classification Search
CPC ....... A61B 2017/320052; A61B 2017/320741; A61B 17/3207; A61B 2017/22061; A61B 17/320016; A61B 17/3209; A61B 2017/22001; A61B 2017/22051; A61M 2025/1086; A61M 25/104; A61M 29/02; A61M 2025/0096; A61M 25/10; A61M 2025/109
USPC .......................... 606/159, 127, 194, 171, 167
See application file for complete search history.

(56) References Cited

U.S. PATENT DOCUMENTS

| | | | |
|---|---|---|---|
| 5,697,944 A * | 12/1997 | Lary | A61B 17/3209 606/159 |
| 5,725,543 A | 3/1998 | Redha | |
| 5,728,123 A * | 3/1998 | Lemelson | A61B 17/320725 606/159 |
| 5,792,158 A * | 8/1998 | Lary | A61B 17/320725 606/159 |
| 2007/0021819 A1 | 1/2007 | Krolik et al. | |
| 2009/0125044 A1 | 5/2009 | Lary | |
| 2012/0302935 A1 | 11/2012 | Miller et al. | |
| 2013/0197515 A1 | 8/2013 | Raybin | |
| 2015/0094715 A1 | 4/2015 | Laufer | |

* cited by examiner

ACTIVE CUTTING CATHETER WITH HOUSED EXPANDABLE ACTUATOR

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

This disclosure pertains to devices for providing endovascular treatment and, in particular, a catheter for actively cutting a vessel wall in a controlled manner, such as for slicing or scoring a lesion associated therewith.

BACKGROUND

Balloon dilatation catheters are used to treat lesions in vessels, such as by way of angioplasty. While successful for use in a variety of applications or locations in the vasculature, some situations call for a different approach in view of the possibility of "elastic recoil," which refers to the inherent resistance of a tissue to changes in shape, and the tendency of the tissue to revert to its original shape once deformed. Furthermore, some applications, and particularly those "below the knee" (BTK) involve hard calcifications, for which balloon angioplasty alone may be contraindicated. Moreover, the use of pharmacological agents on lesions for enhanced treatment may be desirable in some instances, and efficacy may be increased by actively cutting prior to application.

Accordingly, it would be desirable to provide a simple, yet effective apparatus for actively cutting a vessel wall and, in particular, for slicing or scoring a lesion associated therewith. Such a device would be readily useful in a variety of locations in the vasculature, including where particularly hard calcifications might be present, and conditions dictate a more reliable and effective approach than known proposals.

SUMMARY

An object of the invention is to provide an apparatus for endovascular cutting and, in particular, an active cutting catheter for cutting a plaque, lesion, or other obstruction in a vessel that addresses and overcomes the foregoing limitations, and possibly others that have yet to be discovered.

According to one aspect of the disclosure, an apparatus for slicing or scoring a lesion in a vessel is provided. The apparatus includes a catheter including a shaft having a distal portion supporting a housing, the housing including first lateral passage. A cutter is adapted for moving from a retracted position within the housing to a deployed position for at least partially projecting from the first lateral passage. An expandable actuator within the housing is provided for actuating the cutter to move from the retracted position to the deployed position.

In some embodiments, the cutter comprises an elongated body having a blade at a proximal end. The cutter may be pivotably mounted to the housing for moving between the retracted position and the deployed position. A spring may serve to bias the cutter toward the retracted position.

In some embodiments, the expandable actuator comprises an inflatable balloon. A first link may be provided for urging the cutter toward the deployed position when the inflatable balloon is expanded to contact the link. The first link may be rotatably connected to a distal end of the cutter, which distal end remains within the housing in the deployed position of the cutter. A second link may be connected to the first link and rotatably connected to a distal end of the cutter. The second link may include an adjustable projection for pushing the cutter to the deployed position when the inflatable balloon is expanded to engage the first link.

In some embodiments, the housing includes a second lateral passage generally opposite the first lateral passage. In such case, the cutter comprises first and second cutters connected to a common pivot point, the first cutter arranged for deploying through the first lateral passage and the second cutter arranged for simultaneously deploying through the second lateral passage. The actuator may also be adapted for concurrently deploying the first and second cutters to at least partially project through the first and second lateral passages.

According to a further aspect of the disclosure, an apparatus for slicing or scoring a lesion in a vessel. The apparatus comprises a catheter including a shaft having a distal portion supporting a housing, the housing including a lateral passage. A cutter is adapted for moving from a retracted position within the housing to a deployed position for at least partially projecting from the lateral passage. An expandable member within the housing is provided for actuating the cutter to move from the retracted position to the deployed position.

In some embodiments, the cutter comprises an elongated body having a blade at one end. The cutter may be pivotably mounted to the housing for moving between the retracted position and the deployed position. A spring is for biasing the cutter toward the retracted position.

In some embodiments, the expandable member comprises an inflatable balloon, but could comprise any similar structure (such as, for example, an expandable cage, swellable polymer, or the like). The apparatus may further include a first link for urging the cutter toward the deployed position when the inflatable balloon is expanded to contact the first link. The first link may be rotatably connected to a distal end of the cutter, which distal end remains within the housing in the deployed position of the cutter.

In some embodiments, a second link is connected to the first link and rotatably connected to a distal end of the cutter. The second link may include an adjustable projection for pushing the cutter to the deployed position when the inflatable balloon is expanded to engage the first link.

In some embodiments, the housing includes a second lateral passage generally opposite the first lateral passage. In such case, the cutter may comprise first and second cutters connected to a common pivot point, the first cutter arranged for deploying through the first lateral passage and the second cutter arranged for simultaneously deploying through the second lateral passage upon expansion of the inflatable balloon.

According to yet another aspect of the disclosure, an apparatus for slicing or scoring a lesion in a vessel is provided. A catheter includes a shaft having a distal portion supporting a housing, the housing including first and second opposed lateral passages. A first cutter is adapted for moving from a first retracted position within the housing to a first deployed position for at least partially projecting from the first passage. A second cutter is adapted for moving independently of the first cutter from a second retracted position within the housing to a second deployed position for at least partially projecting from the second passage. The apparatus further includes an actuator within the housing for simultaneously actuating the first and second cutters to move from the first and second retracted positions to the first and second deployed positions.

In some embodiments, the actuator comprises an inflatable balloon. A first link may be associated with the first cutter for engaging the inflatable balloon, and a second actuator associated with the second cutter for engaging the inflatable balloon. The first and second cutters may be mounted to pivot about a common pivot point.

In any of the foregoing embodiments, the housing may be dimensionally stable, and thus have a generally fixed size and shape.

BRIEF DESCRIPTION OF THE DRAWING FIGURES

The above and further advantages of the invention according to the disclosure may be better understood by referring to the following description in conjunction with the accompanying drawings in which.

The drawings are not necessarily drawn proportionally or to scale. For example, the dimensions of some of the elements may be exaggerated relative to other elements for clarity or several physical components may be included in one functional block or element. Further, sometimes reference numerals may be repeated among the drawings to indicate corresponding or analogous elements.

DETAILED DESCRIPTION

In the following detailed description, numerous specific details are set forth to provide a thorough understanding of the disclosed concepts. Those of ordinary skill in the art will know that the disclosed inventions may be practiced without these specific details. In other instances, well-known methods, procedures, components, or structures may not have been described in detail so as not to obscure the disclosed inventions.

The description provided below and in regard to the figures applies to all embodiments unless noted otherwise, and features common to each embodiment are similarly shown and numbered.

Figure 1:
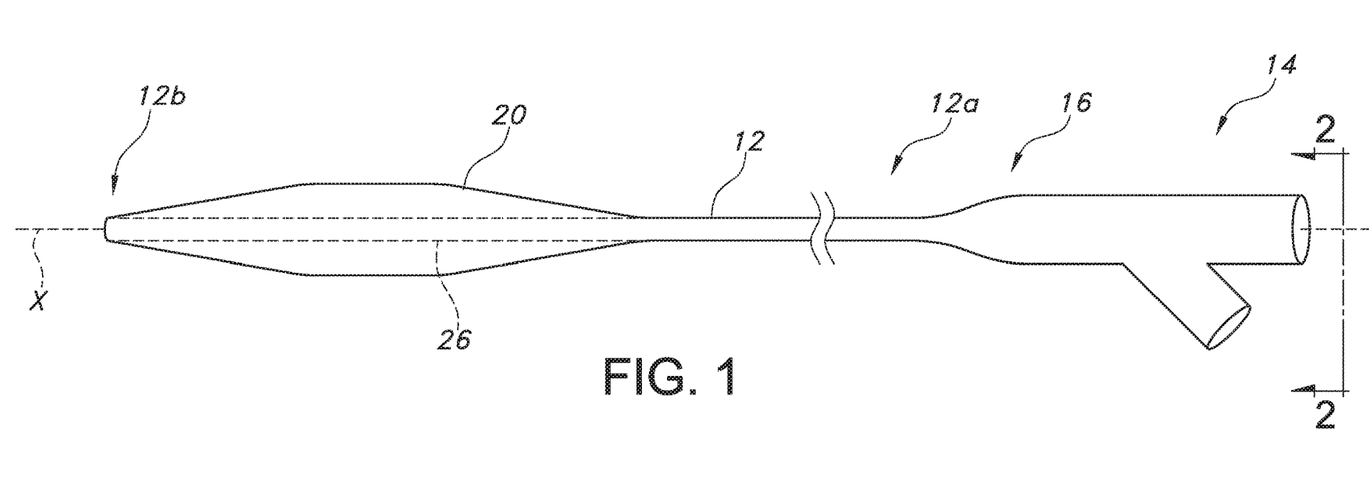
FIG. 1 illustrates one embodiment of an active cutting catheter including a selectively deployable cutter according to the disclosure in a non-deployed position.

Referring first to FIG. 1, an exemplary embodiment of a catheter 10 according to the disclosure is illustrated. The catheter 10 includes an elongated body or shaft 12 having a proximal end 12a and a distal end 12b, which as conventional may be formed of an extruded polymer material (e.g., Pebax, Nylon, PET, etc.). While elongated along a longitudinal axis X and in a corresponding longitudinal direction, the shaft 12 is illustrated in a compact form simply for ease of illustration, and would normally have a considerable length (e.g., 100-200 centimeters, or otherwise suitable to allow the distal end 12b to reach a treatment area of interest in the vasculature while the proximal end 12a remains accessible external to the vasculature).

As illustrated, the proximal end 12a of the shaft 12 may be connected to a hub 14 by way of a connector 16 adapted to provide strain relief. The hub 14 may be a thermoplastic body and may include multiple ports, including one port 14a for receiving a guidewire 18 (FIG. 3) that may pass through a guidewire lumen in the shaft 12, and another port 14b for communicating with an inflation lumen in the shaft. As is conventional, the inflation lumen and guidewire lumen may be coaxial within the shaft 12, or alternatively may be a dual lumen, or side-by-side, approach. Furthermore, the catheter 10 may be an over-the-wire or rapid exchange approach.

The distal end 12b of the shaft 12 may extend though and connect with a housing 20. The housing 20 may comprise a rigid or semirigid, elongated hollow structure, having narrowed or tapered ends for engaging the shaft and an intermediate portion. The housing 20 may comprise a plastic material (e.g., Pebax, Nylon, PET, etc.), and may be braided or loaded with radiopaque material, or may be metal (e.g., Nitinol, stainless steel, titanium, etc.). The housing 20 may be a single unitary piece of material, as shown, or may comprise multiple components. The housing 20 may be dimensionally stable (e.g., having a substantially fixed size and shape) and have a diameter smaller than an associated vessel for receiving it. In any case, the housing 20 does not touch the vessel wall, which may minimize common complications such as dissections and balloon rupture that can occur with percutaneous transluminal angioplasty (PTA) products. The lack of contact also limits the risk associated with dilating healthy tissue in eccentric lesions.

Figure 2:
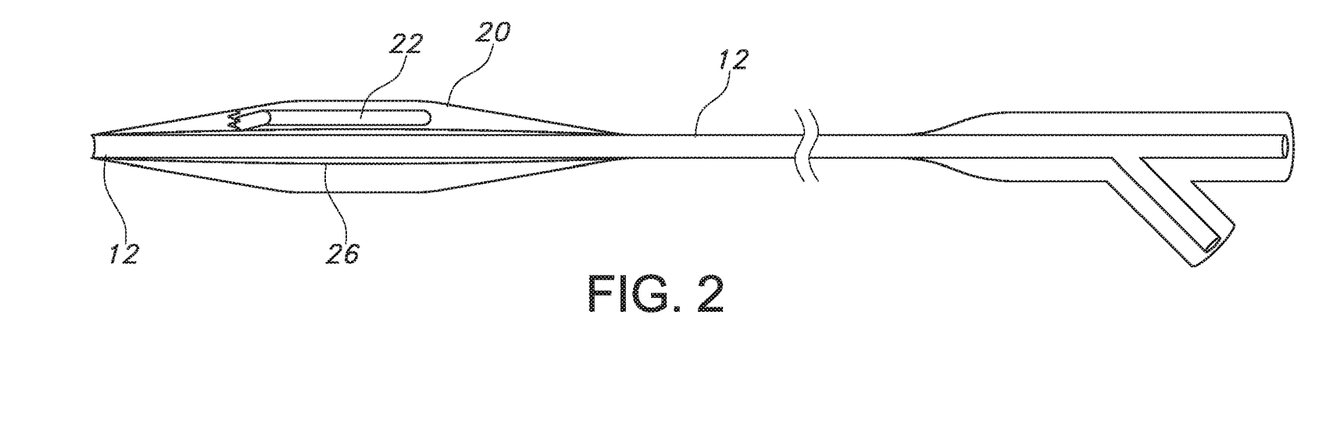
FIG. 2 illustrates a cross-sectional view taken from line 2-2 of FIG. 1.
Figure 3:
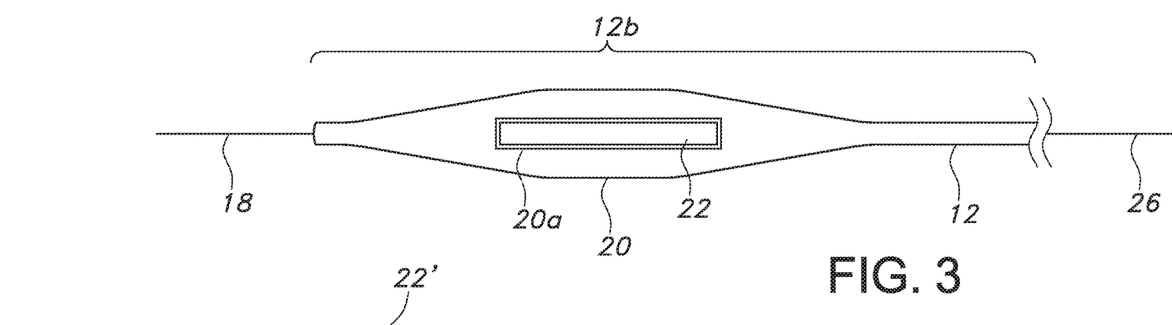
FIG. 3 is a partially cutaway top plan view of the catheter of FIG. 1.

Within the housing 20, such as the portion intermediate the tapered ends, is located a cutter 22, which in a retracted position (as shown in FIG. 2), is entirely within the housing. Once actuated by an actuator also within the housing 20, as outlined in further detail in the following description, the cutter 22 is caused to deploy and alight from a lateral passage formed in a wall of the housing, such as an open channel 20a, as indicated in FIGS. 3, 4, and 5.

In this deployed position, the cutter 22 and, in particular, a cutting edge or blade 22a along a proximal end of an associated body 22b projects from the channel 20a (see cutter 22' in FIG. 4), and thus may be used to cut, slice, or score any object (such as a vessel in which the catheter 10 is located) adjacent to the periphery of the housing 20. The cutter may comprise a plastic or metal material, and may be circular, square, or rectangular in cross-section. Furthermore, the cutter 22 may be serrated or contoured, and may be sharp or dull, depending on the desired treatment effect. Furthermore, the cutter 22 may be associated (e.g., coated) with a drug (e.g., Paclitaxel) for delivery to a vessel wall or lesion during the cutting (e.g., scoring or slicing) process.

As can be appreciated, the catheter 10 with the deployed cutter(s) 22 may be moved about in vivo to perform the slicing or scoring function as necessary or desired, such as by manual manipulation from a point external to the associated body, using the hub 14. When the operation is complete, the actuator may be used to retract the cutter 22, as outlined further in the following description, and the catheter 10 repositioned or withdrawn.

Figure 4:
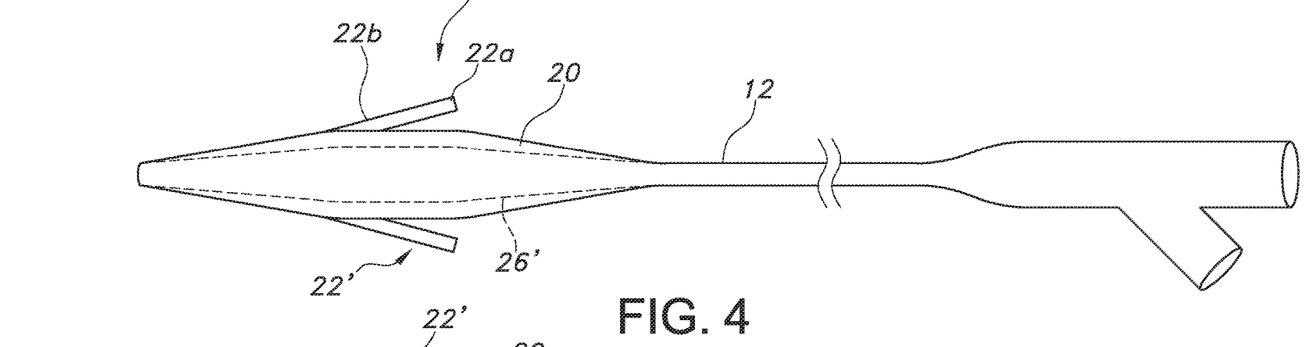
FIG. 4 illustrates the active cutting catheter of FIG. 1 in a deployed position.
Figure 5:
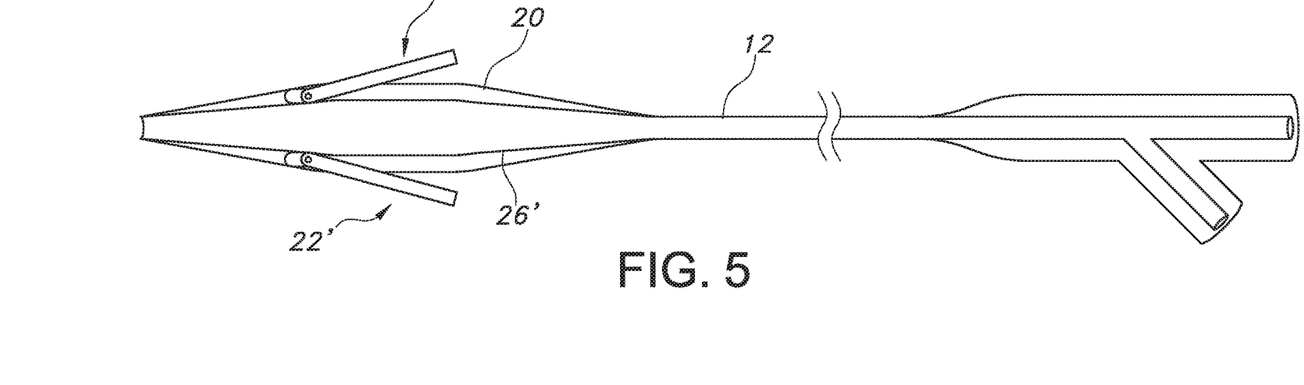
FIG. 5 illustrates a cross-sectional view taken from line 5-5 of FIG. 4.

With continued reference to FIG. 4, it can also be understood that the catheter 10 may include a plurality of cutters. For instance, as illustrated, the cutters (shown as actuated by reference number 22') may be arranged opposite to each other, and project through corresponding channels 20a in the housing 20. In such case, it can further be appreciated that cutting function may be applied simultaneously along multiple sides of the catheter 10.

A variety of modes of actuation may be used for actuating the cutter 22. As one example, and with reference to FIGS. 6 and 7, an actuator 24 may comprise a radially expandable actuator, such as an inflatable balloon 26 contained within the housing 20. The inflatable balloon 26 may be folded or wrapped around a portion of the shaft 12 in an unexpanded condition, and sealed thereto at the proximal and distal ends thereof, as indicated. The balloon 26 may be compliant, non-compliant (fiber-based), or semi-compliant (Nylon, PET, Pebax, etc.).

Figure 6:
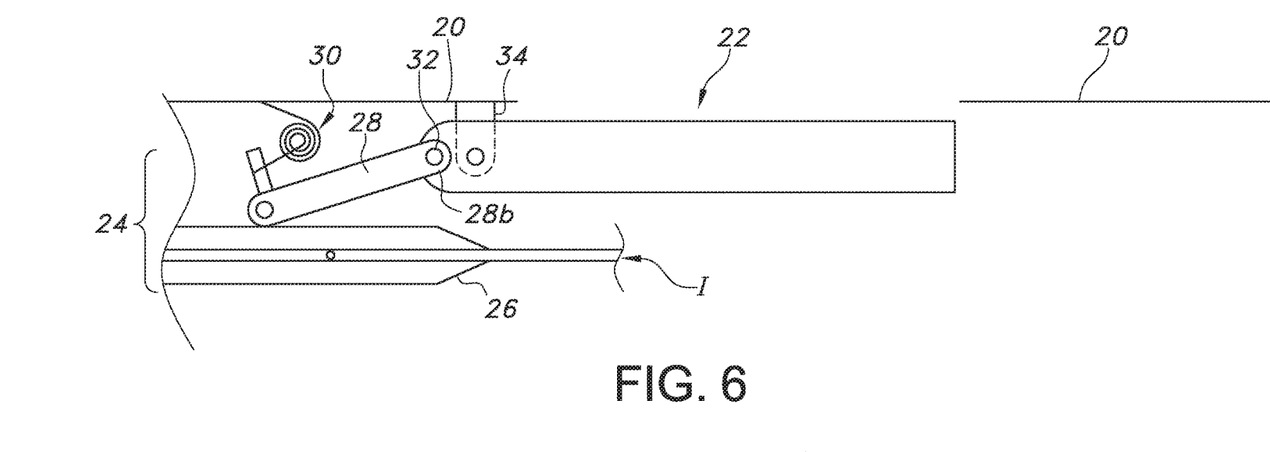
FIG. 6 is a schematic illustration of one embodiment of an actuator according to the disclosure.
Figure 7:
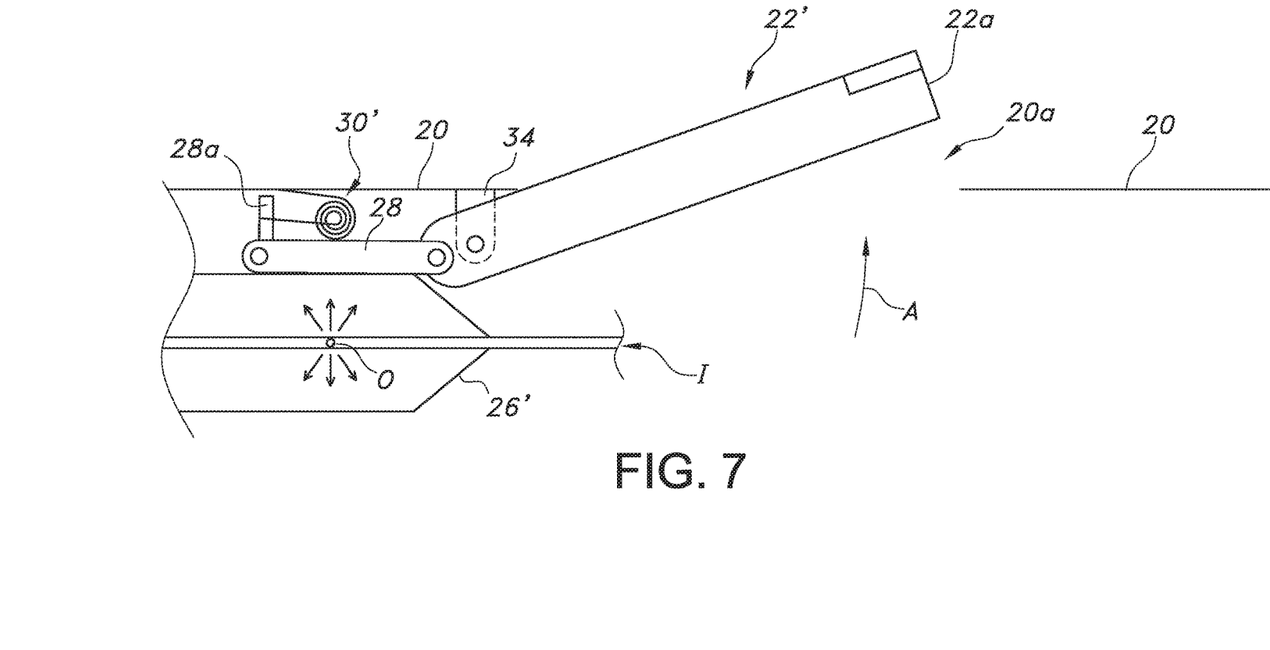
FIG. 7 is a schematic illustration of the actuator of FIG. 6, actuated to move the cutter to a deployed position.

A connector in the form of a link 28 may be provided within a corresponding zone for being engaged by a periphery of the balloon 26 during or upon expansion. The link 28 may be biased into a first position corresponding to a retracted position of the cutter 22, as shown in FIG. 6. The biasing force may be provided by a spring 30, such as a torsion spring. As illustrated, this spring 30 may engage an interior surface of the housing 20 at one end and the link 28 at the other (such as along an extension 28a thereof). An opposite end 28b of the link 28 may be rotatably coupled by a pin 32 to an adjacent end of the cutter body 22b, which in turn may be mounted for pivoting movement relative to the housing 20 (such as by a trunnion 34 connected thereto).

Thus, when the balloon 26 is inflated, such as via an outlet O in the shaft 12 in communication with the inflation lumen I, it expands outwardly (radially) relative to the longitudinal axis X, and thus peripherally engages the link 28 located within the zone of expansion. This in turn overcomes the biasing force normally maintaining the cutter 22 in a retracted position, and causes it to move to a deployed position (see FIG. 7, noting action arrow A and reference numeral 22'). Consequently, at least a portion of the cutter 22 (and, in particular, a tip portion, which as noted may comprise a blade 22a) projects via channel 20a in the housing 20. As can be appreciated, in this position, the cutter 22 is ready for providing the desired active slicing or scoring function, as previously noted.

As can be further appreciated, regulating the degree of expansion of the balloon 26, such as by controlling the amount of inflation fluid provided, allows for the degree of actuation of the cutter 22 to be actively controlled. Yet, for as long as the balloon 26 remains expanded (reference number 26' in FIG. 7), the cutter 22 is maintained in the deployed position, able to perform the slicing or scoring function as intended. When the cutting is complete, the balloon 26 may simply be returned to the unexpanded (e.g., deflated) condition, at which point the spring 30 urges the link 28 toward the initial position shown in FIG. 6, and the cutter 22 returns to the retracted condition.

Figure 8:
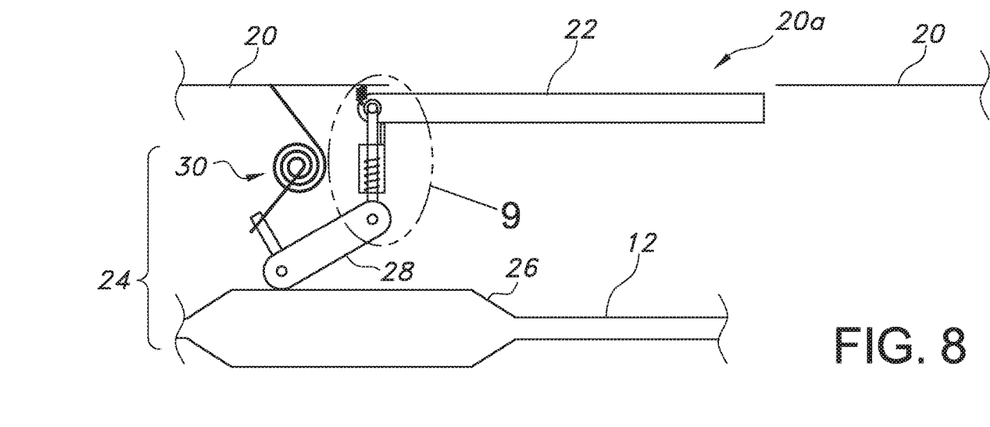
FIGS. 8 and 9 are schematic illustrations of another embodiment of an actuator.
Figure 9:
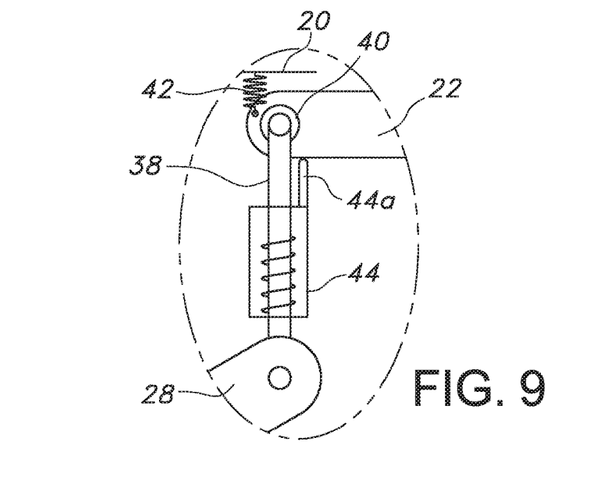

Turning now to FIGS. 8 and 9, a further version of an actuator 24 for the cutter 22 is disclosed. In this version, the spring 30 biases the link 28 into a position for contacting the balloon 26 once expanded. However, a second link 38 extends from the link 28 to the cutter 22, and is rotatably connected to the link 28 by a bearing 40, which allows for relative rotation. A spring 42 also extends between the housing 20 and a corresponding end of the cutter 22, so as to normally urge it to a retracted or home condition.

Figure 10:
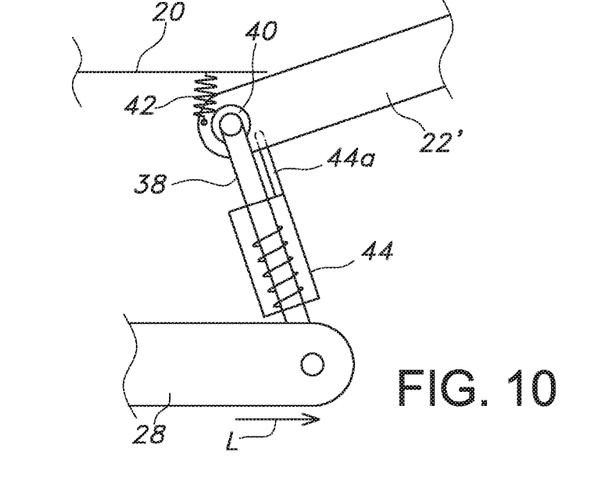
FIG. 10 is a schematic illustration of the actuator of FIGS. 8 and 9, actuated to move the cutter to a deployed position.

Upon expansion of the balloon 26, the link 28 is thus urged to rotation and advance in a linear direction L, which in turn causes the second link 38 to rotate, as can be understood by comparing FIGS. 9 and 10. As illustrated, the second link 38 may include a sleeve 44 with a projection 44a for engaging the cutter 22. Consequently, when the second link 38 rotates, the projection 44a pushes the cutter 22 toward the deployed position (that is, extending through the channel 20a in housing 20, as shown in FIG. 10), thus overcoming the biasing force of spring 42. As shown, the sleeve 44 may be threaded onto the second link 38 to allow for the position of the projection 44a to be adjusted linearly, which thereby controls the degree of cutter deployment. When the balloon 26 returns to the unexpanded condition, the link 28 returns to the home position, which allows the cutter 22 to retract and return to a home location within the housing 20 (as shown in FIG. 8).

In some instances, the balloon 26 could be made super compliant. This would allow the link(s) 28 to oppose and compress the balloon 26 to a certain extent, such that the cutter 22 has a reduced expanded diameter. This would allow it to perhaps more closely match a changing artery inner diameter. The balloon inflation could also change the engagement, including if the balloon were compliant or semi-compliant.

Figure 11:
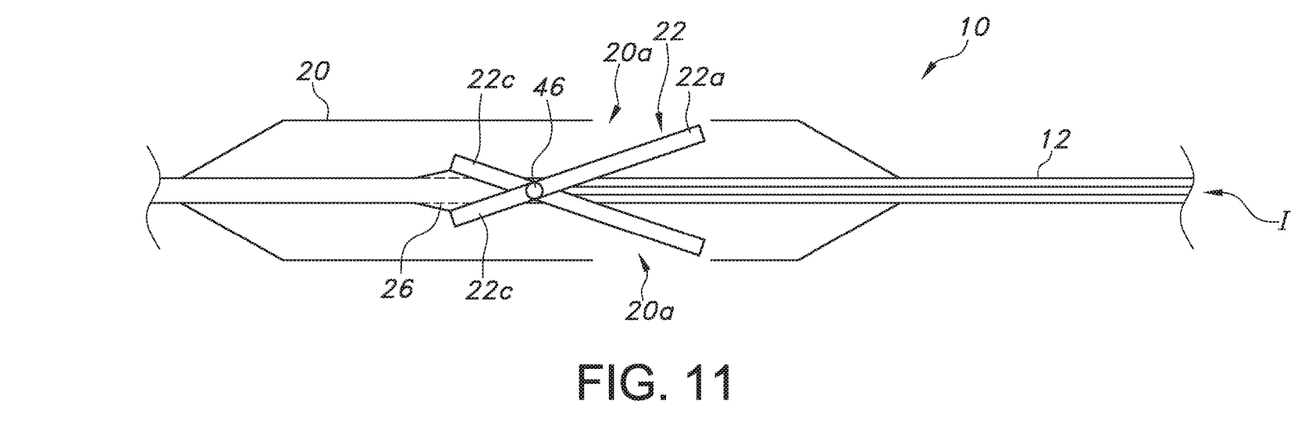
FIGS. 11 and 12 illustrate an alternative embodiment of an active cutting catheter according to the disclosure.
Figure 12:
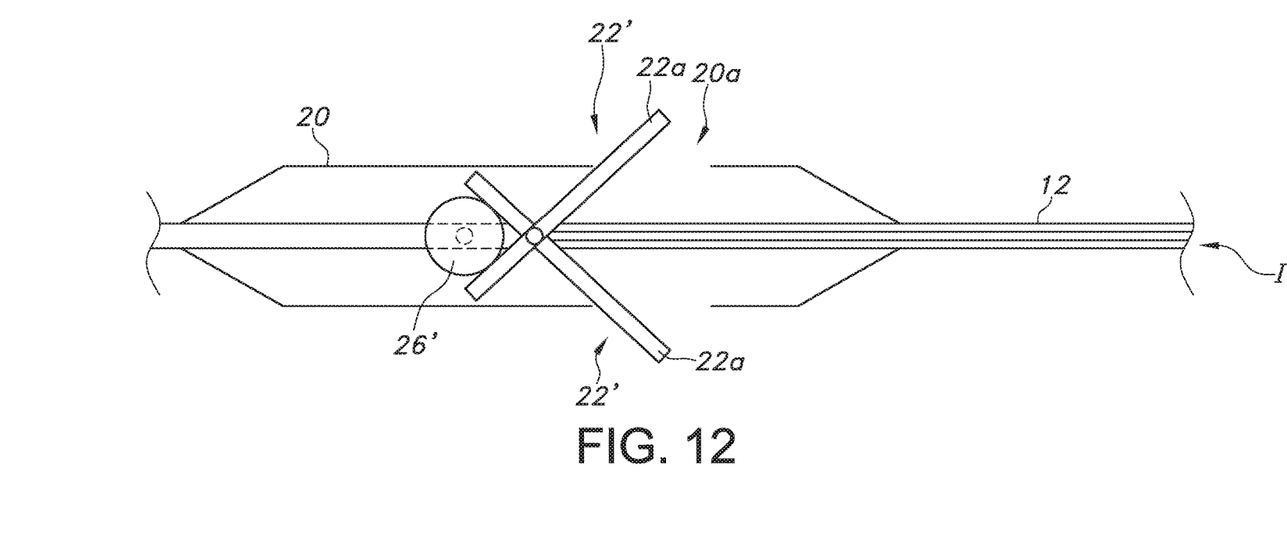

A further embodiment of an active cutting catheter 10 is shown in FIGS. 11 and 12. In this embodiment, a pair of cutters 22 are arranged within the housing 20 in a scissor-like configuration for projecting from corresponding opposed passages, such as elongated channels 20a. This arrangement provides a first cutting end or blade 22a adjacent to the corresponding opposed channels 20a in the housing 20. A second end 22c extends from a common pivot point 46 for the cutters 22 to locate within an expansion zone on either side of an inflatable balloon 26 supported by shaft 12 and in communication with an inflation lumen I.

When the balloon 26 is expanded (reference number 26' in FIG. 12), the periphery of it engages the adjacent ends 22c of the cutters 22. This causes the cutters 22 to pivot about point 46 and deploy (as indicated by reference numeral 22'), and the cutting end or blade 22a to pass through the respective channel 20a in housing 20. The cutters 22 may then be used to slice or score a lesion, and the balloon 26 returned to the unexpanded condition.

In this embodiment, the balloon 26 is shown as being spherical, but may take other forms. In this or other embodiments, the balloon 26 may also be ultra-compliant, meaning that a relatively small amount of inflation pressure causes a rapid and full expansion of the balloon. This may help to ensure that the desired actuation of the cutters 22 may be achieved. As can be appreciated, the orientation of the cutters 22 in all embodiments may also be reversed without consequence (such that the balloon 26 engages proximal portions (including via link 28) and the distal ends include the blades 22a for cutting).

In summary, a catheter 10 for cutting a vessel wall and, in particular, for scoring or slicing a lesion in situ within a vessel, is provided. The catheter 10 would include a dimensionally stable housing 20 with a fixed size and shape for enclosing one or more cutters 22 and an associated actuator, which may include an inflatable balloon 26. Upon actuation, the cutters 22 are caused to extend from the housing 20 to provide the desired scoring or slicing function. De-activation then returns the cutters 22 to a home or retracted position, such that the catheter 10 can be moved to perform a further procedure, or else removed. The self-contained nature of the catheter 10 permits all working parts to remain concealed prior to and during a scoring or slicing procedure, and would allow for seamless insertion and removal with the cutters 22 fully retracted within the housing 20.

The disclosure may be considered to relate to the following items:

1. An apparatus for slicing or scoring a lesion in a vessel, comprising:
a catheter including a shaft having a distal portion supporting a housing, the housing including first lateral passage;
a cutter configured to move from a retracted position within the housing to a deployed position at least partially projecting from the first lateral passage; and
an actuator, such as a radially expandable actuator, within the housing and configured to actuate the cutter to move from the retracted position to the deployed position.

2. The apparatus of item 1, wherein the cutter comprises an elongated body having a blade at a proximal end.
3. The apparatus of item 1 or item 2, wherein the cutter is pivotably mounted to the housing for moving between the retracted position and the deployed position.
4. The apparatus of any of items 1-3, further including a spring for biasing the cutter toward the retracted position.
5. The apparatus of any of items 1-4, wherein the actuator comprises an inflatable balloon.
6. The apparatus of item 5, further comprising a first link for urging the cutter toward the deployed position when the inflatable balloon is expanded to contact the link.
7. The apparatus of item 6, wherein the first link is rotatably connected to a distal end of the cutter, which distal end remains within the housing in the deployed position of the cutter.
8. The apparatus of item 6, further including a second link connected to the first link and rotatably connected to a distal end of the cutter.
9. The apparatus of item 8, wherein the second link includes an adjustable projection for pushing the cutter to the deployed position when the inflatable balloon is expanded to engage the first link.
10. The apparatus of any of items 1-9, wherein the housing includes a second lateral passage generally opposite the first lateral passage, and optionally the cutter comprises first and second cutters connected to a common pivot point, the first cutter arranged for deploying through the first lateral passage and the second cutter arranged for simultaneously deploying through the second lateral passage.
11. The apparatus of item 10, wherein the actuator is adapted for concurrently deploying the first and second cutters to at least partially project through the first and second lateral passages.
12. An apparatus for slicing or scoring a lesion in a vessel, comprising:
a catheter including a shaft having a distal portion supporting a housing, the housing including a lateral passage;
a cutter configured to move from a retracted position within the housing to a deployed position at least partially projecting from the lateral passage; and
an expandable member within the housing configured to actuate the cutter to move from the retracted position to the deployed position.
13. The apparatus of item 12, wherein the cutter comprises an elongated body having a blade at one end.

14. The apparatus of item 12 or item 13, wherein the cutter is pivotably mounted to the housing for moving between the retracted position and the deployed position.
15. The apparatus of any of items 12-14, further including a spring for biasing the cutter toward the retracted position.
16. The apparatus of any of items 12-15, wherein the expandable member comprises an inflatable balloon in fluid communication with an inflation lumen of the shaft.
17. The apparatus of any of items 12-16, further including a first link for urging the cutter toward the deployed position when the expandable member is expanded to contact the first link.
18. The apparatus of item 17, wherein the first link is rotatably connected to a distal end of the cutter, which distal end remains within the housing in the deployed position of the cutter.
19. The apparatus of item 17 or item 18, further including a second link connected to the first link and rotatably connected to a distal end of the cutter.
20. The apparatus of item 19, wherein the second link includes an adjustable projection for pushing the cutter to the deployed position when the inflatable balloon is expanded to engage the first link.
21. The apparatus of any of items 12-20, wherein the housing includes a second lateral passage generally opposite the first lateral passage, and optionally the cutter comprises first and second cutters connected to a common pivot point, the first cutter configured to deploy through the first lateral passage and the second cutter configured to simultaneously deploy through the second lateral passage upon expansion of the inflatable balloon.
22. An apparatus for slicing or scoring a lesion in a vessel, comprising:
a catheter including a shaft having a distal portion supporting a housing, the housing including first and second opposed lateral passages;
a first cutter configured to move from a first retracted position within the housing to a first deployed position at least partially projecting from the first passage;
a second cutter configured to move independently of the first cutter from a second retracted position within the housing to a second deployed position at least partially projecting from the second passage; and
an actuator within the housing and configured to simultaneously actuate the first and second cutters to move from the first and second retracted positions to the first and second deployed positions.
23. The apparatus of item 22, wherein the actuator comprises an inflatable balloon.
24. The apparatus of item 22 or item 23, further including a first link associated with the first cutter for engaging the inflatable balloon and/or a second actuator associated with the second cutter for engaging the inflatable balloon.
25. The apparatus of any of items 22-24, wherein the first and second cutters are mounted to pivot about a common pivot point.
26. The apparatus of any of the foregoing items, wherein the housing is dimensionally stable.

28. The apparatus of any of the foregoing items, wherein the actuator, expandable member, and/or balloon, as applicable, is non-compliant, semi-compliant, or super-compliant.

Each of the following terms written in singular grammatical form: "a", "an", and "the", as used herein, means "at least one", or "one or more". Use of the phrase One or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or the context clearly dictates otherwise. For example, the phrases: "a unit", "a device", "an assembly", "a mechanism", "a component, "an element", and "a step or procedure", as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated components), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase "consisting essentially of." Each of the phrases "consisting of" and "consists of, as used herein, means "including and limited to". The phrase "consisting essentially of means that the stated entity or item (system, system unit, system sub-unit device, assembly, sub-assembly, mechanism, structure, component element or, peripheral equipment utility, accessory, or material, method or process, step or procedure, sub-step or subprocedure), which is an entirety or part of an exemplary embodiment of the disclosed invention, or/and which is used for implementing an exemplary embodiment of the disclosed invention, may include at least one additional feature or characteristic" being a system unit system sub-unit device, assembly, sub-assembly, mechanism, structure, component or element or, peripheral equipment utility, accessory, or material, step or procedure, sub-step or sub-procedure), but only if each such additional feature or characteristic" does not materially alter the basic novel and inventive characteristics or special technical features, of the claimed item.

The term "method", as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Terms of approximation, such as the terms about, substantially, approximately, etc., as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment may also be illustratively described and presented in the context or format of a plurality of separate embodiments.

Although the inventions disclosed have been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

The invention claimed is:

1. An apparatus for slicing or scoring a lesion in a vessel, comprising:
    a catheter including a shaft having a distal portion supporting a housing, the housing including first lateral passage;
    a cutter adapted for moving from a retracted position within the housing to a deployed position for at least partially projecting from the first lateral passage;
    an expandable actuator within the housing for actuating the cutter to move from the retracted position to the deployed position, wherein the expanable actuator comprises an inflatable balloon;
    wherein the cutter is pivotably mounted to the housing about a pivot point external to the expandable actuator for moving between the retracted position and the deployed position;
    further including a first link for urging the cutter toward the deployed position when the inflatable balloon is expanded to contact the first link; and
    further including a second link connected to the first link and rotatably connected to a distal end of the cutter;
    wherein the second link includes an adjustable projection for pushing the cutter to the deployed position when the inflatable balloon is expanded to engage the first link.

2. The apparatus of claim 1, wherein the cutter comprises an elongated body having a blade at a proximal end.

3. The apparatus of claim 1, further including a spring for biasing the cutter toward the retracted position.

4. The apparatus of claim 1, wherein the first link is rotatably connected to a distal end of the cutter, wherein the distal end remains within the housing in the deployed position of the cutter.

5. The apparatus of claim 1, wherein the housing includes a second lateral passage generally opposite the first lateral passage, wherein the cutter comprises first and second cutters, wherein both of the first and second cutters are connected to the pivot point, the first cutter arranged for deploying through the first lateral passage and the second cutter arranged for simultaneously deploying through the second lateral passage.

6. The apparatus of claim 5, wherein the expandable actuator is adapted for concurrently deploying the first and second cutters to at least partially project through the first and second lateral passages.

7. The apparatus of claim 1, wherein the housing is dimensionally stable.

8. An apparatus for slicing or scoring a lesion in a vessel, comprising:
    a catheter including a shaft having a distal portion supporting a housing, the housing including a lateral passage;
    a cutter adapted for moving from a retracted position within the housing to a deployed position for at least partially projecting from the lateral passage;

an expandable member within the housing for actuating the cutter to move from the retracted position to the deployed position;

wherein the cutter is pivotably mounted to the housing about a pivot point external to the expandable member for moving between the retracted position and the deployed position;

further including a first link for urging the cutter toward the deployed position when the expandable member is expanded to contact the first link; and further including a second link connected to the first link and rotatably connected to a distal end of the cutter;

wherein the second link includes an adjustable projection for pushing the cutter to the deployed position when the inflatable balloon is expanded to engage the first link.

9. The apparatus of claim 8, wherein the cutter comprises an elongated body having a blade at one end.

10. The apparatus of claim 8, further including a spring for biasing the cutter toward the retracted position.

11. The apparatus of claim 8, wherein the expandable member comprises an inflatable balloon in fluid communication with an inflation lumen of the shaft.

12. The apparatus of claim 8, wherein the first link is rotatably connected to a distal end of the cutter, wherein the distal end remains within the housing in the deployed position of the cutter.

13. The apparatus of claim 8, wherein the housing includes a second lateral passage generally opposite the first lateral passage, wherein the cutter comprises first and second cutters, wherein both of the first and second cutters are connected to the pivot point, the first cutter arranged for deploying through the first lateral passage and the second cutter arranged for simultaneously deploying through the second lateral passage upon expansion of the inflatable balloon.

* * * * *

UNITED STATES PATENT AND TRADEMARK OFFICE
CERTIFICATE OF CORRECTION

PATENT NO. : 11,896,258 B2
APPLICATION NO. : 17/266683
DATED : February 13, 2024
INVENTOR(S) : Turk et al.

It is certified that error appears in the above-identified patent and that said Letters Patent is hereby corrected as shown below:

In the Claims

Column 10, Claim 1, Line 17, please delete "first lateral" and insert -- a first lateral --.

Column 10, Claim 1, Line 24, please delete "expanable" and insert -- expandable --.

Column 10, Claim 8, Line 63, please delete "a lateral" and insert -- a first lateral --.

Signed and Sealed this
Nineteenth Day of March, 2024

Katherine Kelly Vidal
*Director of the United States Patent and Trademark Office*